(12) United States Patent
Cao et al.

(10) Patent No.: US 11,617,554 B2
(45) Date of Patent: Apr. 4, 2023

(54) IMAGING SYSTEMS USING X-RAY FLUORESCENCE

(71) Applicant: SHENZHEN XPECTVISION TECHNOLOGY CO., LTD., Shenzhen (CN)

(72) Inventors: Peiyan Cao, Shenzhen (CN); Yurun Liu, Shenzhen (CN)

(73) Assignee: SHENZHEN XPECTVISION TECHNOLOGY CO., LTD., Shenzhen (CN)

( * ) Notice: Subject to any disclaimer, the term of this patent is extended or adjusted under 35 U.S.C. 154(b) by 0 days.

(21) Appl. No.: 17/382,628

(22) Filed: Jul. 22, 2021

(65) Prior Publication Data

US 2023/0027440 A1   Jan. 26, 2023

(51) Int. Cl.
*A61B 6/00* (2006.01)
*G01T 1/161* (2006.01)

(52) U.S. Cl.
CPC ............ *A61B 6/485* (2013.01); *A61B 6/5217* (2013.01); *A61B 6/5235* (2013.01); *G01T 1/161* (2013.01)

(58) Field of Classification Search
None
See application file for complete search history.

(56) References Cited

U.S. PATENT DOCUMENTS

2017/0164910 A1*  6/2017  Cao ...................... A61B 6/4275
2021/0113178 A1*  4/2021  Zhou ....................... G01T 1/171

* cited by examiner

*Primary Examiner* — Hoon K Song
(74) *Attorney, Agent, or Firm* — IPro, PLLC; Qian Gu

(57) ABSTRACT

Disclosed herein is a method, comprising: causing emission of characteristic X-rays of a chemical element in an object by directing radiation to the object; capturing images of the object using the radiation that has transmitted through the object; capturing images of the chemical element in the object using the characteristic X-rays; reconstructing a three-dimensional image of the object based on the images of the object; determining a three-dimensional distribution of the chemical element in the object based on the images of the chemical element; and superposing the three-dimensional image of the object and the three-dimensional distribution of the chemical element in the object to form a superposed image of the object. The radiation directed to the object comes from multiple radiation sources. The images are captured with multiple image sensors. The radiation sources and the image sensors are stationary with respect to the object.

22 Claims, 8 Drawing Sheets

IMAGING SYSTEMS USING X-RAY FLUORESCENCE

BACKGROUND

A radiation detector is a device that measures a property of a radiation. Examples of the property may include a spatial distribution of the intensity, phase, and polarization of the radiation. The radiation measured by the radiation detector may be a radiation that has transmitted through an object. Alternatively, the radiation measured by the radiation detector may be characteristic X-rays emitted by an element in the object via X-ray fluorescence (XRF). XRF is the emission of characteristic X-rays from the element that has been excited by, for example, exposure to high-energy X-rays or gamma rays.

The radiation measured by the radiation detector may be an electromagnetic radiation such as infrared light, visible light, ultraviolet light, X-ray, or γ-ray. The radiation may be of other types such as α-rays and β-rays. An imaging system may include one or more image sensors each of which may have one or more radiation detectors.

SUMMARY

Disclosed herein is a method, comprising: causing emission of characteristic X-rays of a chemical element in an object by directing radiation to the object; capturing M images of the object using the radiation that has transmitted through the object; capturing N images of the chemical element in the object using the characteristic X-rays; reconstructing a three-dimensional image of the object based on the M images; determining a three-dimensional distribution of the chemical element in the object based on the N images; and superposing the three-dimensional image of the object and the three-dimensional distribution of the chemical element in the object to form a superposed image of the object, wherein the radiation directed to the object comes from P radiation sources, wherein the M images and the N images are captured by Q image sensors, wherein the P radiation sources and the Q image sensors are stationary with respect to the object, and wherein M, N, P, and Q are integers greater than 1.

In an aspect, the object comprises a portion of a human body.

In an aspect, M=N=P=Q.

In an aspect, the P radiation sources comprise respectively P metal target regions, and said directing the radiation to the object comprises bombarding the P metal target regions with electron beams.

In an aspect, the P radiation sources are arranged around the object such that a first circle intersects all the P radiation sources.

In an aspect, the P radiation sources are evenly spaced on the first circle.

In an aspect, the Q image sensors are arranged around the object such that a second circle intersects all the Q image sensors.

In an aspect, the Q image sensors are evenly spaced on the second circle.

In an aspect, the chemical element is rhenium or iodine.

In an aspect, an image of the M images and two images of the N images are simultaneously captured.

In an aspect, said capturing the N images uses only the characteristic X-rays.

Disclosed herein is a system, comprising: P radiation sources configured to cause emission of characteristic X-rays of a chemical element in an object by generating and directing radiation to the object; and Q image sensors configured to capture: (i) M images of the object using the radiation that has transmitted through the object, and (ii) N images of the chemical element in the object using the characteristic X-rays, wherein the system is configured to: (A) reconstruct a three-dimensional image of the object based on the M images, (B) determine a three-dimensional distribution of the chemical element in the object based on the N images, and (C) superpose the three-dimensional image of the object and the three-dimensional distribution of the chemical element in the object to form a superposed image of the object, wherein the P radiation sources and the Q image sensors are stationary with respect to the object, and wherein M, N, P, and Q are integers greater than 1.

In an aspect, the object comprises a portion of a human body.

In an aspect, M=N=P=Q.

In an aspect, the P radiation sources comprise respectively P metal target regions, and said generating and directing the radiation to the object comprises bombarding the P metal target regions with electron beams.

In an aspect, the P radiation sources are arranged around the object such that a first circle intersects all the P radiation sources.

In an aspect, the P radiation sources are evenly spaced on the first circle.

In an aspect, the Q image sensors are arranged around the object such that a second circle intersects all the Q image sensors.

In an aspect, the Q image sensors are evenly spaced on the second circle.

In an aspect, the chemical element is rhenium or iodine.

In an aspect, an image of the M images and two images of the N images are simultaneously captured.

Disclosed herein is a computer program product comprising a non-transitory computer readable medium having instructions recorded thereon, the instructions when executed by a computer implementing any of the method described herein.

DETAILED DESCRIPTION

Radiation Detector

Figure 1:
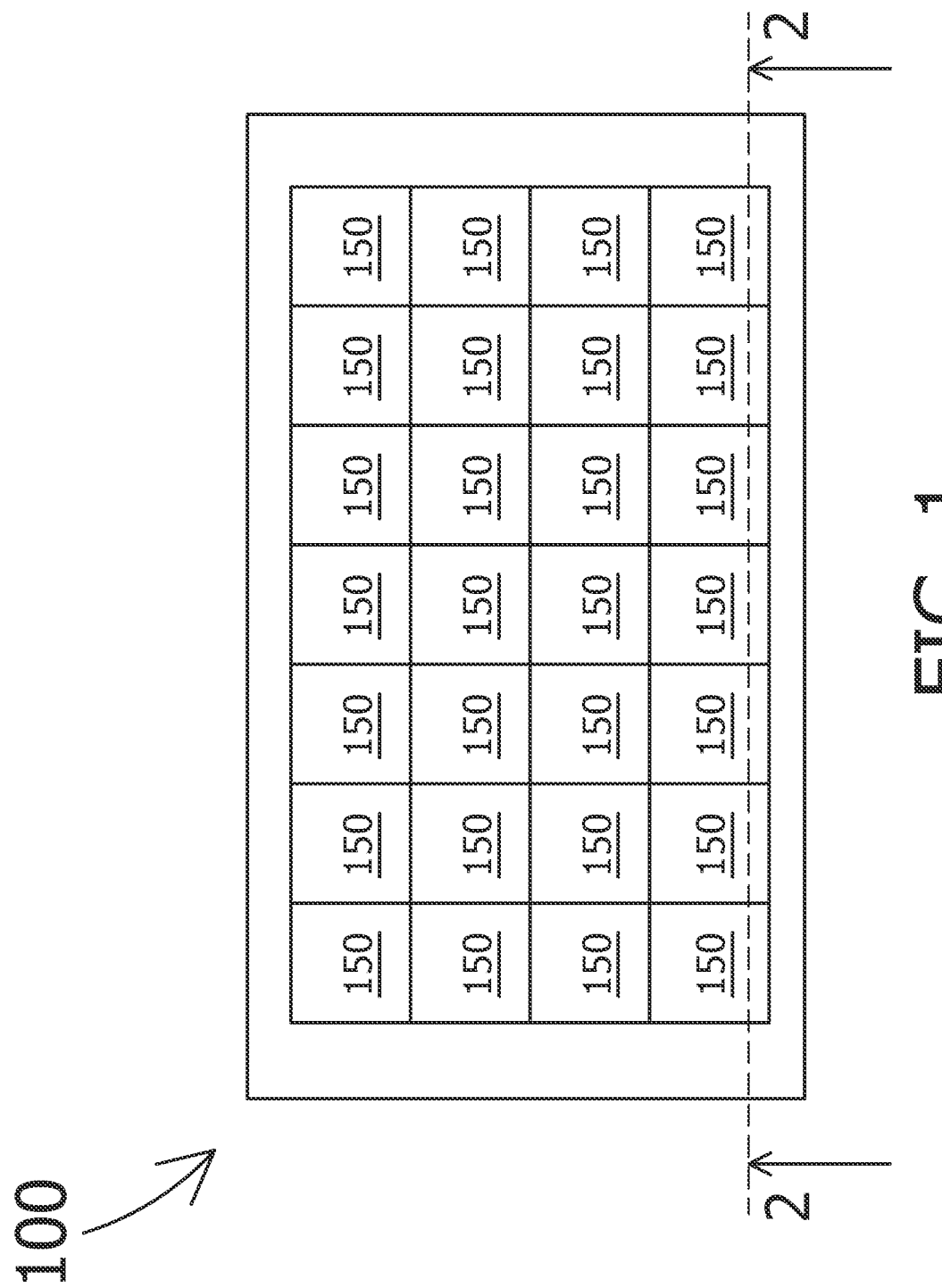
FIG. 1 schematically shows a radiation detector, according to an embodiment.

FIG. 1 schematically shows a radiation detector 100, as an example. The radiation detector 100 may include an array of pixels 150 (also referred to as sensing elements 150). The array may be a rectangular array (as shown in FIG. 1), a honeycomb array, a hexagonal array, or any other suitable array. The array of pixels 150 in the example of FIG. 1 has 4 rows and 7 columns; however, in general, the array of pixels 150 may have any number of rows and any number of columns.

Each pixel 150 may be configured to detect radiation from a radiation source (not shown) incident thereon and may be configured to measure a characteristic (e.g., the energy of the particles, the wavelength, and the frequency) of the radiation. A radiation may include particles such as photons and subatomic particles. Each pixel 150 may be configured to count numbers of particles of radiation incident thereon whose energy falls in a plurality of bins of energy, within a period of time. All the pixels 150 may be configured to count the numbers of particles of radiation incident thereon within a plurality of bins of energy within the same period of time. When the incident particles of radiation have similar energy, the pixels 150 may be simply configured to count numbers of particles of radiation incident thereon within a period of time, without measuring the energy of the individual particles of radiation.

Each pixel 150 may have its own analog-to-digital converter (ADC) configured to digitize an analog signal representing the energy of an incident particle of radiation into a digital signal, or to digitize an analog signal representing the total energy of a plurality of incident particles of radiation into a digital signal. The pixels 150 may be configured to operate in parallel. For example, when one pixel 150 measures an incident particle of radiation, another pixel 150 may be waiting for a particle of radiation to arrive. The pixels 150 may not have to be individually addressable.

The radiation detector 100 described here may have applications such as in an X-ray telescope, X-ray mammography, industrial X-ray defect detection, X-ray microscopy or microradiography, X-ray casting inspection, X-ray non-destructive testing, X-ray weld inspection, X-ray digital subtraction angiography, etc. It may be suitable to use this radiation detector 100 in place of a photographic plate, a photographic film, a PSP plate, an X-ray image intensifier, a scintillator, or another semiconductor X-ray detector.

Figure 2:
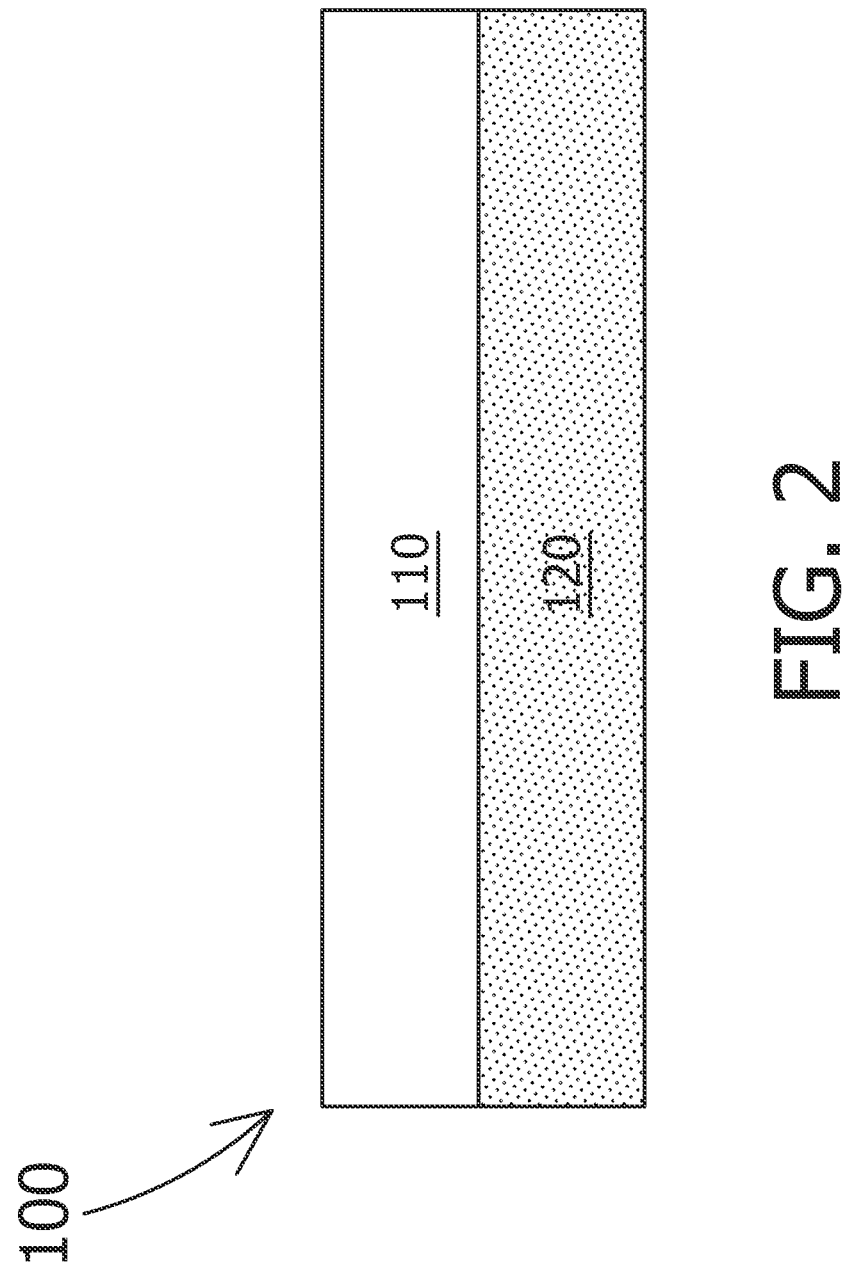
FIG. 2 schematically shows a simplified cross-sectional view of the radiation detector, according to an embodiment.

FIG. 2 schematically shows a simplified cross-sectional view of the radiation detector 100 of FIG. 1 along a line 2-2, according to an embodiment. Specifically, the radiation detector 100 may include a radiation absorption layer 110 and an electronics layer 120 (which may include one or more ASICs or application-specific integrated circuits) for processing or analyzing electrical signals which incident radiation generates in the radiation absorption layer 110. The radiation detector 100 may or may not include a scintillator (not shown). The radiation absorption layer 110 may include a semiconductor material such as silicon, germanium, GaAs, CdTe, CdZnTe, or a combination thereof. The semiconductor material may have a high mass attenuation coefficient for the radiation of interest.

Figure 3:
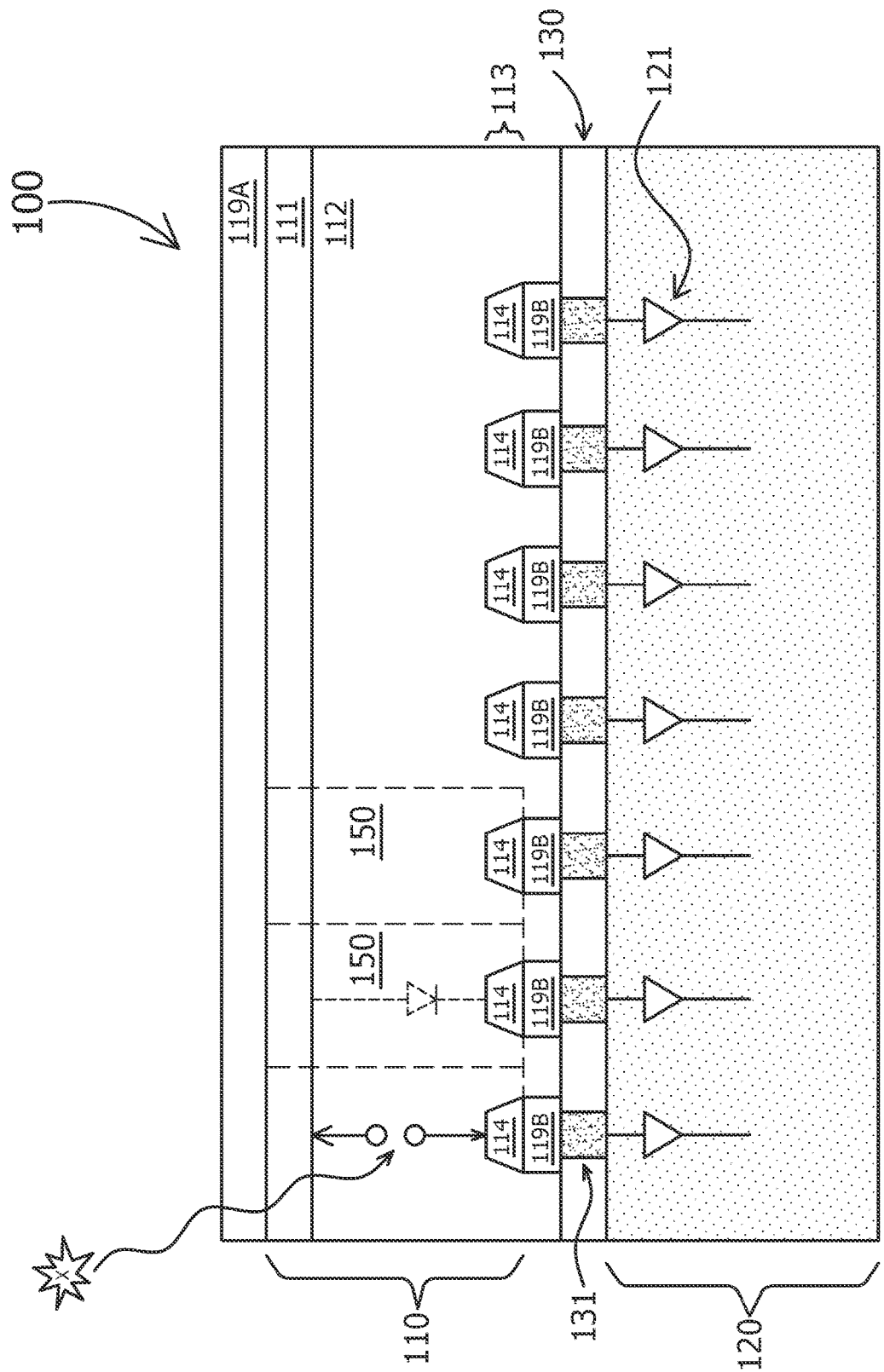
FIG. 3 schematically shows a detailed cross-sectional view of the radiation detector, according to an embodiment.

FIG. 3 schematically shows a detailed cross-sectional view of the radiation detector 100 of FIG. 1 along the line 2-2, as an example. Specifically, the radiation absorption layer 110 may include one or more diodes (e.g., p-i-n or p-n) formed by a first doped region 111, one or more discrete regions 114 of a second doped region 113. The second doped region 113 may be separated from the first doped region 111 by an optional intrinsic region 112. The discrete regions 114 may be separated from one another by the first doped region 111 or the intrinsic region 112. The first doped region 111 and the second doped region 113 may have opposite types of doping (e.g., region 111 is p-type and region 113 is n-type, or region 111 is n-type and region 113 is p-type). In the example of FIG. 3, each of the discrete regions 114 of the second doped region 113 forms a diode with the first doped region 111 and the optional intrinsic region 112. Namely, in the example in FIG. 3, the radiation absorption layer 110 has a plurality of diodes (more specifically, 7 diodes corresponding to 7 pixels 150 of one row in the array of FIG. 1, of which only 2 pixels 150 are labeled in FIG. 3 for simplicity). The plurality of diodes may have an electrical contact 119A as a shared (common) electrode. The first doped region 111 may also have discrete portions.

The electronics layer 120 may include an electronic system 121 suitable for processing or interpreting signals generated by the radiation incident on the radiation absorption layer 110. The electronic system 121 may include an analog circuitry such as a filter network, amplifiers, integrators, and comparators, or a digital circuitry such as a microprocessor, and memory. The electronic system 121 may include one or more ADCs (analog to digital converters). The electronic system 121 may include components shared by the pixels 150 or components dedicated to a single pixel 150. For example, the electronic system 121 may include an amplifier dedicated to each pixel 150 and a microprocessor shared among all the pixels 150. The electronic system 121 may be electrically connected to the pixels 150 by vias 131. Space among the vias may be filled with a filler material 130, which may increase the mechanical stability of the connection of the electronics layer 120 to the radiation absorption layer 110. Other bonding techniques are possible to connect the electronic system 121 to the pixels 150 without using the vias 131.

When radiation from the radiation source (not shown) hits the radiation absorption layer 110 including diodes, particles of the radiation may be absorbed and generate one or more charge carriers (e.g., electrons, holes) by a number of mechanisms. The charge carriers may drift to the electrodes of one of the diodes under an electric field. The electric field may be an external electric field. The electrical contact 119B may include discrete portions each of which is in electrical contact with the discrete regions 114. The term "electrical contact" may be used interchangeably with the word "electrode." In an embodiment, the charge carriers may drift in directions such that the charge carriers generated by a single particle of the radiation are not substantially shared by two different discrete regions 114 ("not substantially shared" here means less than 2%, less than 0.5%, less than 0.1%, or less than 0.01% of these charge carriers flow to a different one of the discrete regions 114 than the rest of the charge carriers). Charge carriers generated by a particle of the radiation incident around the footprint of one of these discrete regions 114 are not substantially shared with another of these discrete regions 114. A pixel 150 associated with a discrete region 114 may be an area around the discrete region 114 in which substantially all (more than 98%, more than 99.5%, more than 99.9%, or more than 99.99% of) charge carriers generated by a particle of the radiation incident therein flow to the discrete region 114. Namely, less than 2%, less than 1%, less than 0.1%, or less than 0.01% of these charge carriers flow beyond the pixel 150.

Figure 4:
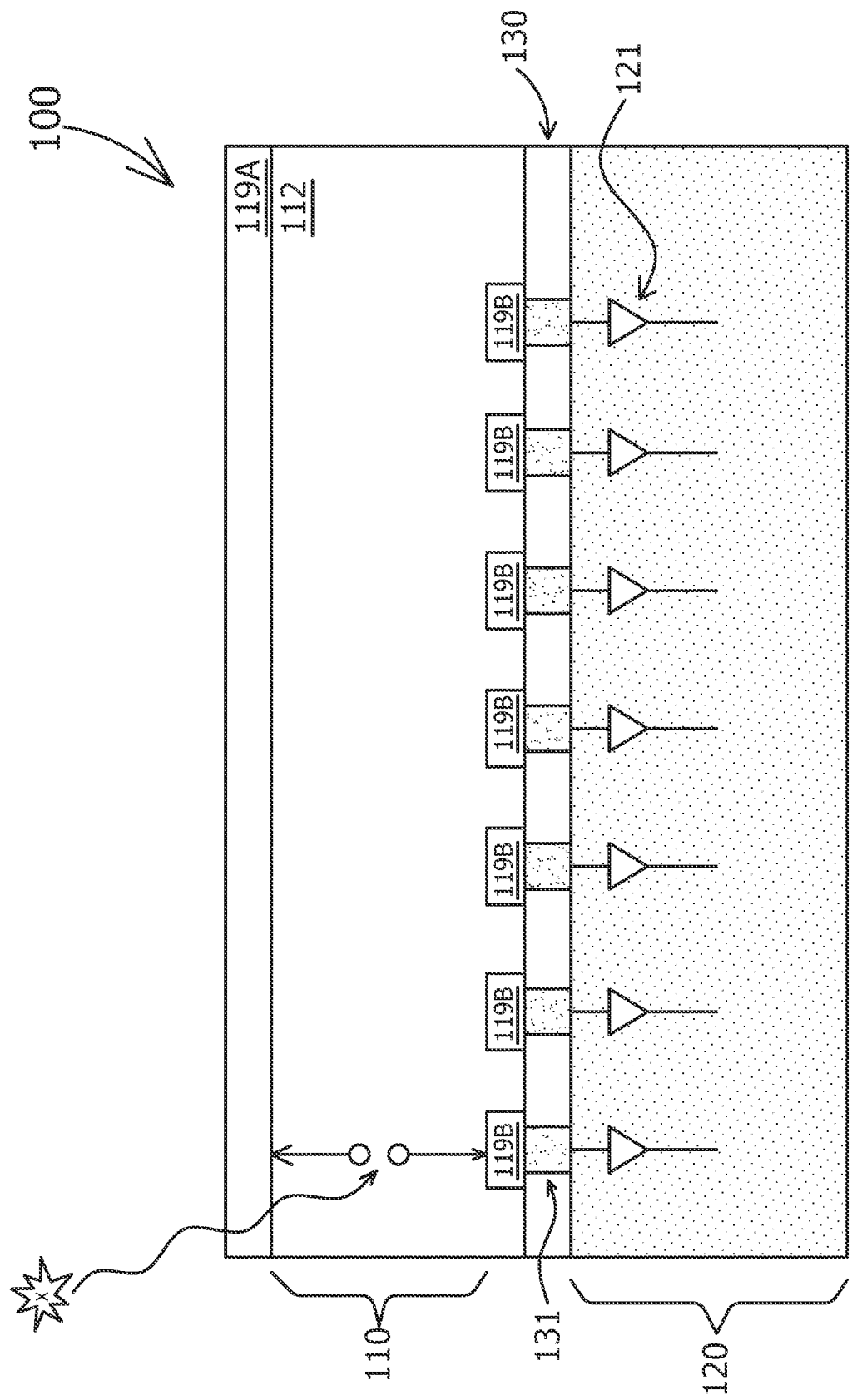
FIG. 4 schematically shows a detailed cross-sectional view of the radiation detector, according to an alternative embodiment.

FIG. 4 schematically shows a detailed cross-sectional view of the radiation detector 100 of FIG. 1 along the line 2-2, according to an alternative embodiment. More specifically, the radiation absorption layer 110 may include a resistor of a semiconductor material such as silicon, germanium, GaAs, CdTe, CdZnTe, or a combination thereof, but does not include a diode. The semiconductor material may have a high mass attenuation coefficient for the radiation of interest. In an embodiment, the electronics layer 120 of FIG. 4 is similar to the electronics layer 120 of FIG. 3 in terms of structure and function.

When the radiation hits the radiation absorption layer 110 including the resistor but not diodes, it may be absorbed and generate one or more charge carriers by a number of mechanisms. A particle of the radiation may generate 10 to 100,000 charge carriers. The charge carriers may drift to the electrical contacts 119A and 119B under an electric field. The electric field may be an external electric field. The electrical contact 119B may include discrete portions. In an embodiment, the charge carriers may drift in directions such that the charge carriers generated by a single particle of the radiation are not substantially shared by two different discrete portions of the electrical contact 119B ("not substantially shared" here means less than 2%, less than 0.5%, less than 0.1%, or less than 0.01% of these charge carriers flow to a different one of the discrete portions than the rest of the charge carriers). Charge carriers generated by a particle of the radiation incident around the footprint of one of these discrete portions of the electrical contact 119B are not substantially shared with another of these discrete portions of the electrical contact 119B. A pixel 150 associated with a discrete portion of the electrical contact 119B may be an area around the discrete portion in which substantially all (more than 98%, more than 99.5%, more than 99.9% or more than 99.99% of) charge carriers generated by a particle of the radiation incident therein flow to the discrete portion of the electrical contact 119B. Namely, less than 2%, less than 0.5%, less than 0.1%, or less than 0.01% of these charge carriers flow beyond the pixel associated with the one discrete portion of the electrical contact 119B.

Radiation Detector Package

Figure 5:
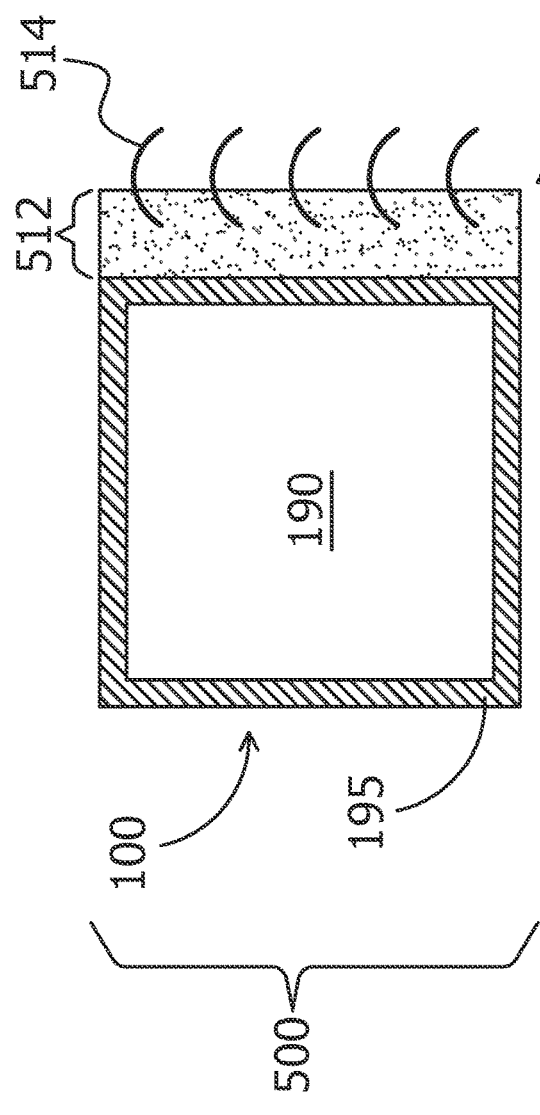
FIG. 5 schematically shows a top view of a package including the radiation detector and a printed circuit board (PCB), according to an embodiment.

FIG. 5 schematically shows a top view of a package 500 including the radiation detector 100 and a printed circuit board (PCB) 510. The term "PCB" as used herein is not limited to a particular material. For example, a PCB may include a semiconductor. The radiation detector 100 may be mounted to the PCB 510. The wiring between the radiation detector 100 and the PCB 510 is not shown for the sake of clarity. The PCB 510 may have one or more radiation detectors 100. The PCB 510 may have an area 512 not covered by the radiation detector 100 (e.g., for accommodating bonding wires 514). The radiation detector 100 may have an active area 190 which is where the pixels 150 (FIG. 1) are located. The radiation detector 100 may have a perimeter zone 195 near the edges of the radiation detector 100. The perimeter zone 195 has no pixels 150, and the radiation detector 100 does not detect particles of radiation incident on the perimeter zone 195.

Image Sensor

Figure 6A:
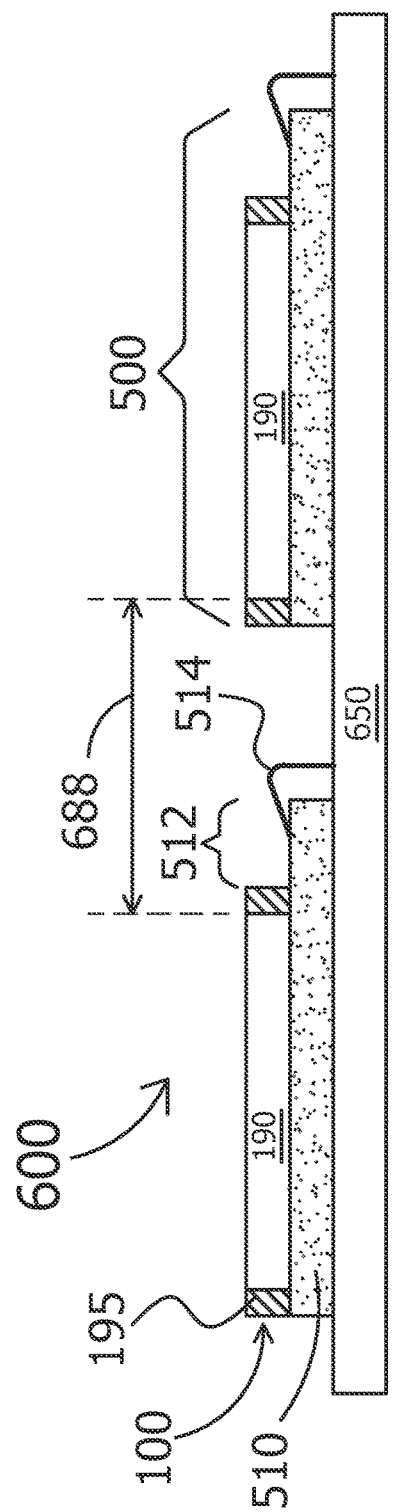
FIG. 6A schematically shows a cross-sectional view of an image sensor including the packages of FIG. 5 mounted to a system PCB (printed circuit board), according to an embodiment.

FIG. 6A schematically shows a cross-sectional view of an image sensor 600, according to an embodiment. The image sensor 600 may include one or more packages 500 of FIG. 5 mounted to a system PCB 650. FIG. 6A shows 2 packages 500 as an example. The electrical connection between the PCBs 510 and the system PCB 650 may be made by bonding wires 514. In order to accommodate the bonding wires 514 on the PCB 510, the PCB 510 may have the area 512 not covered by the radiation detector 100. In order to accommodate the bonding wires 514 on the system PCB 650, the packages 500 may have gaps in between. The gaps may be approximately 1 mm or more. Particles of radiation incident on the perimeter zones 195, on the area 512, or on the gaps cannot be detected by the packages 500 on the system PCB 650. A dead zone of a radiation detector (e.g., the radiation detector 100) is the area of the radiation-receiving surface of the radiation detector, on which incident particles of radiation cannot be detected by the radiation detector. A dead zone of a package (e.g., package 500) is the area of the radiation-receiving surface of the package, on which incident particles of radiation cannot be detected by the radiation detector or detectors in the package. In this example shown in FIG. 5 and FIG. 6A, the dead zone of the package 500 includes the perimeter zones 195 and the area 512. A dead zone (e.g., 688) of an image sensor (e.g., image sensor 600) with a group of packages (e.g., packages 500 mounted on the same PCB and arranged in the same layer or in different layers) includes the combination of the dead zones of the packages in the group and the gaps between the packages.

In an embodiment, the radiation detector 100 (FIG. 1) operating by itself may be considered an image sensor. In an embodiment, the package 500 (FIG. 5) operating by itself may be considered an image sensor.

The image sensor 600 including the radiation detectors 100 may have the dead zone 688 among the active areas 190 of the radiation detectors 100. However, the image sensor 600 may capture multiple partial images of an object or scene (not shown), and then these captured partial images may be stitched to form an image of the entire object or scene.

Figure 6B:
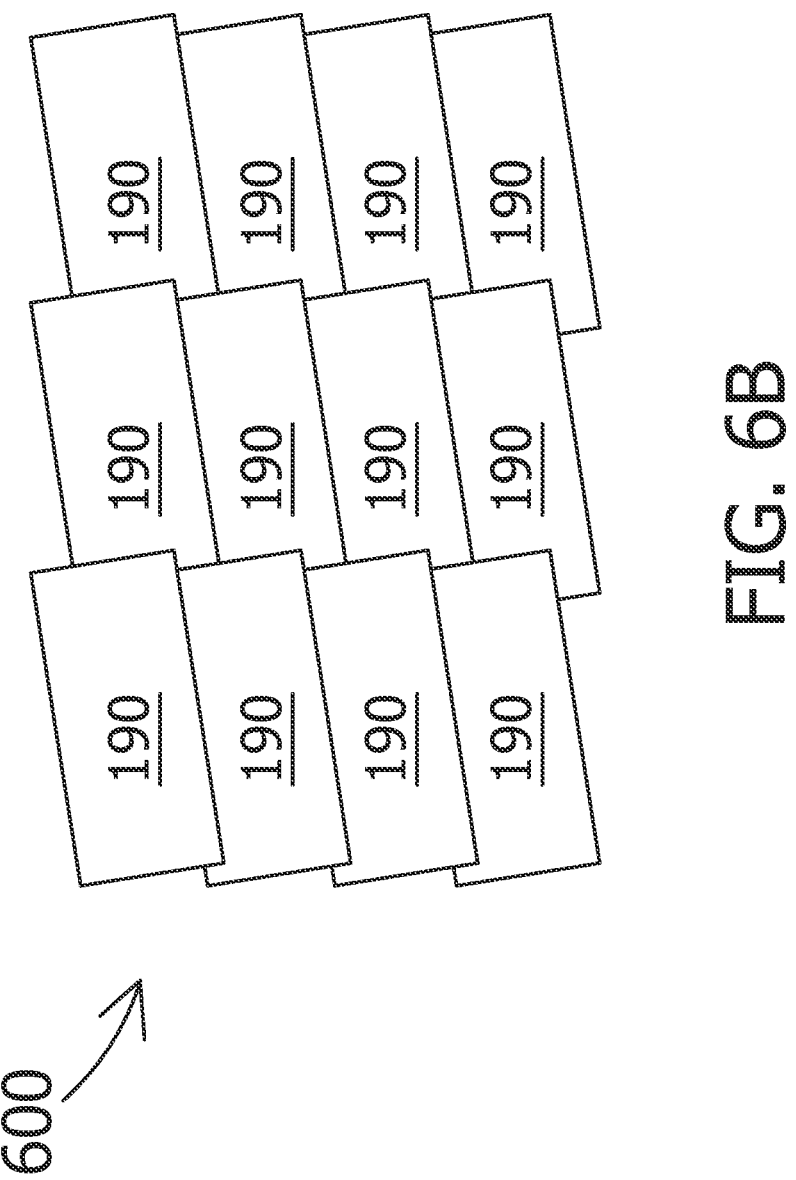
FIG. 6B schematically shows a top view of the image sensor, according to an alternative embodiment.

FIG. 6B schematically shows a top view of the image sensor 600, according to an alternative embodiment. In this alternative embodiment, the image sensor 600 may include multiple radiation detectors 100 arranged in an overlapping manner such that there is no dead zone 688 (FIG. 6A) among the active areas 190 of the radiation detectors 100. For simplicity, only the active areas 190 of the radiation detectors 100 are shown in FIG. 6B.

Imaging Process

Initial System Arrangement

Figure 7A:
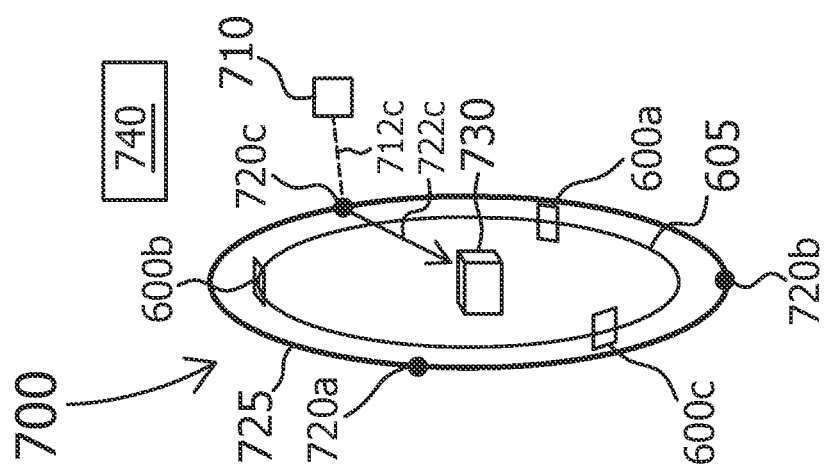
FIG. 7A-FIG. 7C schematically show perspective views of an imaging system in operation, according to an embodiment.
Figure 7B:
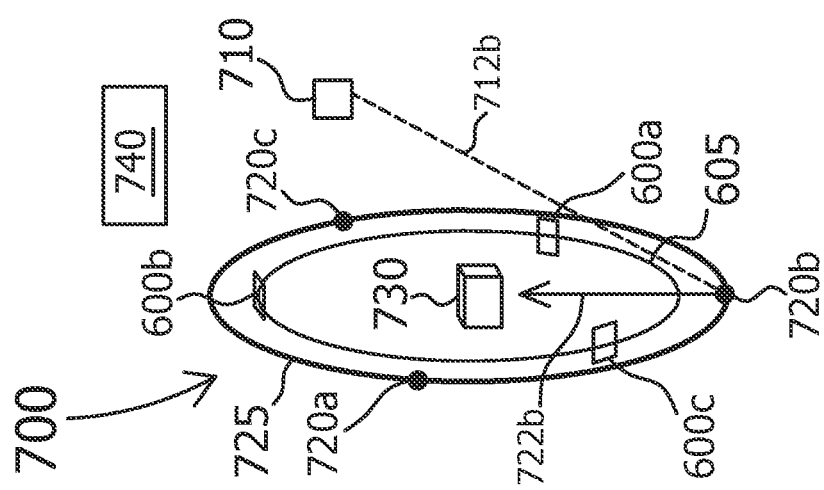
Figure 7C:
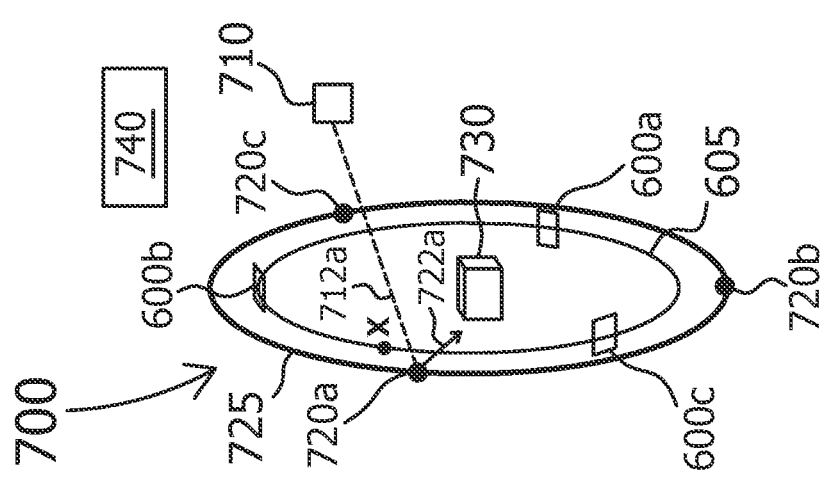

FIG. 7A-FIG. 7C schematically show perspective views of an imaging system 700 in operation, according to an embodiment. In an embodiment, the imaging system 700 may include a bombardment beam generator 710, a target 725, an image sensor system 600a+600b+600c, and a processor 740.

In an embodiment, the bombardment beam generator 710 may be configured to generate bombardment beams (e.g., electron beams) toward the target 725.

In an embodiment, the target 725 may have the shape of a circle as shown. In an embodiment, there may be 3 target spots 720a, 720b, and 720c on the surface of the target 725. In an embodiment, a circle may intersect all the target spots 720a, 720b, and 720c. The target spots 720a, 720b, and 720c may be evenly spaced on the circle.

In an embodiment, each of the target spots 720a, 720b, and 720c may be a metal target region on the surface of the target 725 that is to receive bombardment particles (e.g., electrons) from the bombardment beam generator 710. The 3 dark circles representing the 3 target spots 720a, 720b, and 720c indicate just roughly the locations of the target spots 720a, 720b, and 720c on the target 725 and do not necessarily indicate the sizes, shapes, or orientations of the target spots 720a, 720b, and 720c.

In an embodiment, the target 725 may be made of copper or tungsten. The target 725 may be one-piece as shown. Alternatively, the target 725 may include multiple separate pieces (not shown).

In an embodiment, the image sensor system 600a+600b+600c may include 3 image sensors 600a, 600b, and 600c which may be similar to the image sensor 600 of FIG. 6A or FIG. 6B. The 3 parallelograms representing the image sensors 600a, 600b, and 600c indicate just roughly the locations and orientations of the image sensors 600a, 600b, and 600c and do not necessarily indicate the sizes and shapes of the image sensors 600a, 600b, and 600c.

In an embodiment, the image sensors 600a, 600b, and 600c may be physically fixed to a circular rail 605 as shown. In an embodiment, a circle may intersect all the image sensors 600a, 600b, and 600c. The image sensors 600a, 600b, and 600c may be evenly spaced on the circle.

In an embodiment, a portion 730 of a human body (not shown for simplicity) and the imaging system 700 may be arranged such that when bombardment beams (e.g., electron beams) from the bombardment beam generator 710 bombard the target 725 at the target spots 720a, 720b, and 720c, radiation beams (e.g., X-rays) emit from the target spots 720a, 720b, and 720c and propagate toward the portion 730 and then toward the image sensors 600a, 600b, and 600c respectively.

In an embodiment, the portion 730 may contain a chemical element (e.g., rhenium, or iodine) which is to emit characteristic X-rays (e.g., by fluorescence) when the chemical element is radiated by the radiation beams from the target spots 720a, 720b, and 720c.

In an embodiment, the chemical element may be introduced into the portion 730 of the human body orally in pills or liquids, or by injection into muscles or bloodstreams. The chemical element may be a non-radioactive chemical element. The chemical element may be bound to a ligand.

In an embodiment, the target spots 720a, 720b, and 720c may be stationary with respect to the object during the operation of the imaging system 700 in imaging the portion 730. In an embodiment, image sensors 600a, 600b, and 600c may be stationary with respect to the portion 730 during the operation of the imaging system 700 in imaging the portion 730.

In an embodiment, the processor 740 may be electrically coupled to the image sensors 600a, 600b, and 600c and configured to process the images captured by the image sensors 600a, 600b, and 600c.

First Transmission Image Capture

In an embodiment, with reference to FIG. 7A, a first transmission image capture may be performed as follows. The bombardment beam generator 710 may generate a bombardment beam 712a toward the target spot 720a on the target 725 thereby causing the emission of a radiation beam 722a from the target spot 720a toward the portion 730. Using the radiation of the radiation beam 722a that has transmitted through the portion 730, the image sensor 600a may capture a first transmission image of the portion 730.

First XRF Image Capture

In an embodiment, a first XRF image capture may be performed as follows. The radiation beam 722a from the target spot 720a causes the chemical element in the portion 730 to emit characteristic X-rays. Using the characteristic X-rays emitted from the chemical element in the portion 730, the image sensor 600b may capture a first XRF image of the chemical element in the portion 730.

In an embodiment, the image sensor 600b may be configured to use only the characteristic X-rays emitted from the chemical element in the portion 730 and ignore incident radiation of the radiation beam 722a in capturing the first XRF image of the chemical element in the portion 730.

Second Transmission Image Capture

In an embodiment, after the first transmission image and the first XRF image are captured, with reference to FIG. 7B, a second transmission image capture may be performed as follows. The bombardment beam generator 710 may generate a bombardment beam 712b toward the target spot 720b on the target 725 thereby causing the emission of a radiation beam 722b from the target spot 720b toward the portion 730. Using the radiation of the radiation beam 722b that has transmitted through the portion 730, the image sensor 600b may capture a second transmission image of the portion 730.

Second XRF Image Capture

In an embodiment, a second XRF image capture may be performed as follows. The radiation beam 722b from the target spot 720b causes the chemical element in the portion 730 to emit characteristic X-rays. Using the characteristic X-rays emitted from the chemical element in the portion 730, the image sensor 600c may capture a second XRF image of the chemical element in the portion 730.

In an embodiment, the image sensor 600c may be configured to use only the characteristic X-rays emitted from the chemical element in the portion 730 and ignore incident radiation of the radiation beam 722b in capturing the second XRF image of the chemical element in the portion 730.

Third Transmission Image Capture

In an embodiment, after the second transmission image and the second XRF image are captured, with reference to FIG. 7C, a third transmission image capture may be performed as follows. The bombardment beam generator 710 may generate a bombardment beam 712c toward the target spot 720c on the target 725 thereby causing the emission of a radiation beam 722c from the target spot 720c toward the portion 730. Using the radiation of the radiation beam 722c that has transmitted through the portion 730, the image sensor 600c may capture a third transmission image of the portion 730.

Third XRF Image Capture

In an embodiment, a third XRF image capture may be performed as follows. The radiation beam 722c from the target spot 720c causes the chemical element in the portion 730 to emit characteristic X-rays. Using the characteristic X-rays emitted from the chemical element in the portion 730, the image sensor 600a may capture a third XRF image of the chemical element in the portion 730.

In an embodiment, the image sensor 600a may be configured to use only the characteristic X-rays emitted from the chemical element in the portion 730 and ignore incident radiation of the radiation beam 722c in capturing the third XRF image of the chemical element in the portion 730.

Three-Dimensional Image of the Portion

In an embodiment, after the first, second, and third transmission images are captured as described above, a three-dimensional image of the portion 730 may be reconstructed based on the first, second, and third transmission images of the portion 730. In an embodiment, the reconstruction of the three-dimensional image of the portion 730 based on the first, second, and third transmission images may be performed by the processor 740.

Three-Dimensional Distribution of the Chemical Element in the Portion

In an embodiment, after the first, second, and third XRF images are captured as described above, a three-dimensional distribution of the chemical element in the portion 730 may be determined based on the first, second, and third XRF images. In an embodiment, the determination of the three-dimensional distribution of the chemical element in the portion 730 based on the first, second, and third XRF images may be performed by the processor 740.

Superposed Image

In an embodiment, the three-dimensional image of the portion 730 and the three-dimensional distribution of the chemical element in the portion 730 may be superposed to form a superposed image of the portion 730. In an embodiment, the three-dimensional image of the portion 730 and the three-dimensional distribution of the chemical element in the portion 730 may be superposed by the processor 740. In an embodiment, various suitable superposing algorithms may be applied.

Flowchart for Generalization

Figure 8:
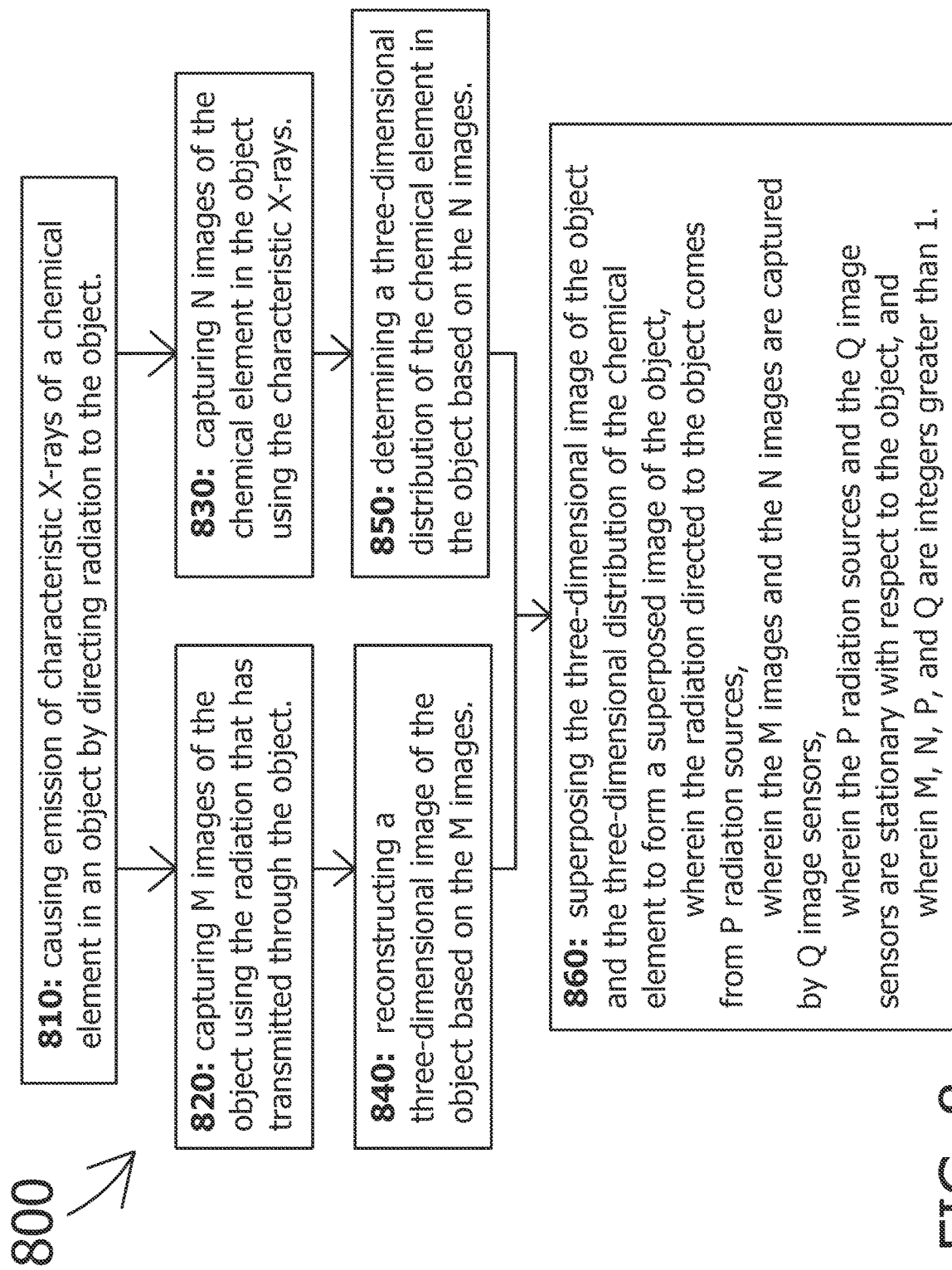
FIG. 8 shows a flowchart generalizing the operation of the imaging system.

FIG. 8 shows a flowchart 800 generalizing the operation of the imaging system 700 described above. In step 810, emission of characteristic X-rays of a chemical element in an object is caused by directing radiation to the object. For example, in the embodiments described above, with reference to FIG. 7A-FIG. 7C, the emission of characteristic X-rays of the chemical element (rhenium, or iodine) in the portion 730 is caused by directing the radiation beams 722a, 722b, and 722c to the portion 730.

In step 820, M images of the object are captured using the radiation that has transmitted through the object. For example, in the embodiments described above, the first, second, and third transmission images are captured using respectively the radiations of the radiation beams 722a, 722b, and 722c that have transmitted through the portion 730.

In step 830, N images of the chemical element in the object are captured using the characteristic X-rays. For example, in the embodiments described above, the first, second, and third XRF images of the chemical element in the portion 730 are captured using the characteristic X-rays emitted from the chemical element in the portion 730.

In step 840, a three-dimensional image of the object is reconstructed based on the M images. For example, in the embodiments described above, the three-dimensional image of the portion 730 is reconstructed based on the first, second, and third transmission images of the portion 730.

In step 850, a three-dimensional distribution of the chemical element in the object is determined based on the N images. For example, in the embodiments described above, the three-dimensional distribution of the chemical element in the portion 730 is determined based on the first, second, and third XRF images of the chemical element in the portion 730.

In step 860, the three-dimensional image of the object and the three-dimensional distribution of the chemical element in the object are superposed to form a superposed image of the object. For example, in the embodiments described above, the three-dimensional image of the portion 730 and the three-dimensional distribution of the chemical element in the portion 730 are superposed to form the superposed image of the portion 730.

In addition, in step 860, the radiation directed to the object comes from P radiation sources. For example, in the embodiments described above, the radiation beams 722a, 722b, and 722c directed to the portion 730 come from target spots 720a, 720b, and 720c, respectively (i.e., P=3).

In addition, in step 860, the M images and the N images are captured by Q image sensors. For example, in the embodiments described above, the first, second, and third transmission images (i.e., M=3) and the first, second, and third XRF images (i.e., N=3) are captured by the image sensors 600a, 600b, and 600c (i.e., Q=3).

In addition, in step 860, the P radiation sources and the Q image sensors are stationary with respect to the object. For example, in the embodiments described above, the target spots 720a, 720b, and 720c and the image sensors 600a, 600b, and 600c are stationary with respect to the portion 730.

In addition, in step 860, M, N, P, and Q are integers greater than 1. For example, in the embodiments described above, M=3; N=3; P=3; and Q=3.

Alternative Embodiments

In the embodiments described above, a transmission image and an XRF image are simultaneously captured. For example, the first transmission image and the first XRF image are simultaneously captured by the image sensor 600a and 600b respectively. In an alternative embodiment, a transmission image and two XRF images may be simultaneously captured. For example, while the image sensor 600a captures the first transmission image using the radiation of the radiation beam 722a that has transmitted through the portion 730 as described above, the image sensors 600b and 600c may simultaneously capture the first and second XRF images respectively using the characteristic X-rays emitted from the chemical element in the portion 730.

In the embodiments described above, the number of image sensors is the same as the number of target spots (both numbers are three). In an alternative embodiment, the number of image sensors may be higher than the number of target spots. For example, with reference to FIG. 7A, a fourth image sensor (not shown) may be added on the circular rail 605 between the image sensors 600b and 600c and near the target spot 720a (e.g., at point X).

In an embodiment, while the image sensor 600b captures the first XRF image of the chemical element in the portion 730 using the characteristic X-rays emitted from the chemical element in the portion 730, the fourth image sensor at point X may capture a fourth XRF image of the chemical element in the portion 730 using also the characteristic X-rays emitted from the chemical element in the portion 730.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:
1. A method, comprising:
    causing emission of characteristic X-rays of a chemical element in an object by directing radiation to the object;
    capturing M images of the object using the radiation that has transmitted through the object;
    capturing N images of the chemical element in the object using the characteristic X-rays;
    reconstructing a three-dimensional image of the object based on the M images;

determining a three-dimensional distribution of the chemical element in the object based on the N images; and superposing the three-dimensional image of the object and the three-dimensional distribution of the chemical element in the object to form a superposed image of the object, wherein the radiation directed to the object comes from P radiation sources, wherein the M images and the N images are captured by Q image sensors, wherein the P radiation sources and the Q image sensors are stationary with respect to the object, and wherein M, N, P, and Q are integers greater than 1.

2. The method of claim 1, wherein the object comprises a portion of a human body.

3. The method of claim 1, wherein M=N=P=Q.

4. The method of claim 1,
wherein the P radiation sources comprise respectively P metal target regions, and
wherein said directing the radiation to the object comprises bombarding the P metal target regions with electron beams.

5. The method of claim 1, wherein the P radiation sources are arranged around the object such that a first circle intersects all the P radiation sources.

6. The method of claim 5, wherein the P radiation sources are evenly spaced on the first circle.

7. The method of claim 1, wherein the Q image sensors are arranged around the object such that a second circle intersects all the Q image sensors.

8. The method of claim 7, wherein the Q image sensors are evenly spaced on the second circle.

9. The method of claim 1, wherein the chemical element is rhenium or iodine.

10. The method of claim 1, wherein an image of the M images and two images of the N images are simultaneously captured.

11. The method of claim 1, wherein said capturing the N images uses only the characteristic X-rays.

12. A system, comprising:
P radiation sources configured to cause emission of characteristic X-rays of a chemical element in an object by generating and directing radiation to the object; and
Q image sensors configured to capture:
(i) M images of the object using the radiation that has transmitted through the object, and
(ii) N images of the chemical element in the object using the characteristic X-rays,
wherein the system is configured to:
(A) reconstruct a three-dimensional image of the object based on the M images,
(B) determine a three-dimensional distribution of the chemical element in the object based on the N images, and
(C) superpose the three-dimensional image of the object and the three-dimensional distribution of the chemical element in the object to form a superposed image of the object,
wherein the P radiation sources and the Q image sensors are stationary with respect to the object, and
wherein M, N, P, and Q are integers greater than 1.

13. The system of claim 12, wherein the object comprises a portion of a human body.

14. The system of claim 12, wherein M=N=P=Q.

15. The system of claim 12,
wherein the P radiation sources comprise respectively P metal target regions, and
wherein said generating and directing the radiation to the object comprises bombarding the P metal target regions with electron beams.

16. The system of claim 12, wherein the P radiation sources are arranged around the object such that a first circle intersects all the P radiation sources.

17. The system of claim 16, wherein the P radiation sources are evenly spaced on the first circle.

18. The system of claim 12, wherein the Q image sensors are arranged around the object such that a second circle intersects all the Q image sensors.

19. The system of claim 18, wherein the Q image sensors are evenly spaced on the second circle.

20. The system of claim 12, wherein the chemical element is rhenium or iodine.

21. The system of claim 12, wherein an image of the M images and two images of the N images are simultaneously captured.

22. A computer program product comprising a non-transitory computer readable medium having instructions recorded thereon, the instructions when executed by a computer implementing the method of claim 1.

* * * * *